United States Patent

Webster, Jr. et al.

[11] Patent Number: 6,064,905
[45] Date of Patent: May 16, 2000

[54] MULTI-ELEMENT TIP ELECTRODE MAPPING CATHETER

[75] Inventors: Wilton W. Webster, Jr., Baldwin Park; Dean M. Ponzi, Glendora, both of Calif.

[73] Assignee: Cordis Webster, Inc., Diamond Bar, Calif.

[21] Appl. No.: 09/099,796

[22] Filed: Jun. 18, 1998

[51] Int. Cl.[7] .............................. A61B 5/06; A61B 5/05
[52] U.S. Cl. .......................... 600/424; 600/374; 600/509
[58] Field of Search .................................. 600/374, 424, 600/509; 607/122, 125

[56] References Cited

U.S. PATENT DOCUMENTS

| | | |
|---|---|---|
| Re. 34,502 | 1/1994 | Webster, Jr. . |
| 3,920,021 | 11/1975 | Hiltebrandt . |
| 4,848,352 | 7/1989 | Pohndorf et al. ........................ 607/122 |
| 4,960,134 | 10/1990 | Webster, Jr. . |
| 5,242,441 | 9/1993 | Avitall . |
| 5,318,525 | 6/1994 | West et al. . |
| 5,383,852 | 1/1995 | Stevens-Wright . |
| 5,391,199 | 2/1995 | Ben-haim . |
| 5,398,683 | 3/1995 | Edwards et al. . |
| 5,431,168 | 7/1995 | Webster, Jr. . |
| 5,443,489 | 8/1995 | Ben-haim . |
| 5,454,370 | 10/1995 | Avitall . |
| 5,462,544 | 10/1995 | Saksena et al. . |
| 5,489,270 | 2/1996 | van Erp . |
| 5,500,012 | 3/1996 | Brucker et al. . |
| 5,546,951 | 8/1996 | Ben-haim . |
| 5,549,108 | 8/1996 | Edwards et al. . |
| 5,555,883 | 9/1996 | Avitall . |
| 5,558,091 | 9/1996 | Acker et al. . |
| 5,568,809 | 10/1996 | Ben-haim . |
| 5,617,854 | 4/1997 | Munsif . |
| 5,636,634 | 6/1997 | Kordis et al. . |
| 5,666,970 | 9/1997 | Smith . |
| 5,715,832 | 2/1998 | Koblish et al. . |
| 5,729,129 | 3/1998 | Acker . |
| 5,730,704 | 3/1998 | Avitall . |
| 5,755,664 | 5/1998 | Rubenstein . |
| 5,755,760 | 5/1998 | Maguire et al. . |
| 5,836,875 | 11/1998 | Webster, Jr. . |
| 5,843,076 | 12/1998 | Webster, Jr. et al. . |
| 5,860,974 | 1/1999 | Abele ...................................... 607/122 |
| 5,897,529 | 4/1999 | Ponzi ........................................ 604/95 |
| 5,916,163 | 6/1999 | Panescu et al. .......................... 600/374 |
| 5,935,079 | 8/1999 | Swanson et al. ........................ 607/122 |

FOREIGN PATENT DOCUMENTS

571797  12/1983  European Pat. Off. .

*Primary Examiner*—William E. Kamm
*Assistant Examiner*—Carl H. Layno
*Attorney, Agent, or Firm*—Christie, Parker & Hale, LLP

[57] ABSTRACT

A mapping catheter comprises a catheter body, a handle and a tip section. The catheter body has an outer wall, proximal and distal ends and at least one lumen extending therethrough. The handle is at the proximal end of the catheter body. The tip section comprises a flexible tubing having proximal and distal ends and at least one lumen extending therethrough. The proximal end of the flexible tubing is fixedly attached to the distal end of the catheter body. The tip section comprises an electromagnetic sensor for producing electrical signals indicative of the location of the electromagnetic sensor. The tip section further comprises a multi-element tip electrode mounted at the distal end of the tip section comprising a plurality of electrode members electrically isolated from one another and arranged such that, during use of the catheter within the heart, at least two different electrode members are capable of contacting the endocardium tissue at one time. An electromagnetic sensor cable electrically connect the electromagnetic sensor and extends through the tip section, catheter body and handle for carrying electrical signals from the electromagnetic sensor to a circuit board. The catheter further comprises a plurality of electrode lead wires, each lead wire being electrically corrected to an electrode member and extending through the tubing, catheter body and handle.

12 Claims, 10 Drawing Sheets

MULTI-ELEMENT TIP ELECTRODE MAPPING CATHETER

FIELD OF THE INVENTION

The present invention relates to steerable catheters for mapping the direction and velocity of electrical activity in the heart.

BACKGROUND OF THE INVENTION

Information about the location of electrical activity of the heart is generally useful in ablation procedures. If a physician can map the electrical activity of the heart, the physician can then ablate accessory electrical pathways causing an abnormal heart beat, for example, ventricular tachycardia. The more information a physician can obtain about the electrical activity of the heart, the better able the physician is to ablate only that tissue necessary to cure the abnormal heartbeat.

SUMMARY OF THE INVENTION

The present invention provides a mapping catheter and catheter system capable of providing information about the contours of the heart chambers and the strength, direction and speed of electrical signals propagating through the myocardium. Through the use of the present invention, a physician can better pinpoint precisely the location where the myocardium should be ablated to eliminate accessory electrical pathways which lead to abnormal heart rhythms.

In one embodiment, the invention is directed to a mapping catheter. The catheter comprises a catheter body, a handle and a tip section. The catheter body has an outer wall, proximal and distal ends and at least one lumen extending therethrough. The handle is mounted at the proximal end of the catheter body. The tip section comprises a flexible tubing having proximal and distal ends and at least one lumen extending therethrough. The proximal end of the flexible tubing is fixedly attached to the distal end of the catheter body. The tip section further comprises an electromagnetic sensor for producing electrical signals indicative of the location of the electromagnetic sensor. The sensor is electrically connected to an electromagnetic sensor cable that extends through the tip section, catheter body and handle for carrying electrical signals from the electromagnetic sensor to a circuit board. The circuit board is electrically connected to an appropriate monitor capable of recording the signals and providing a map of the heart.

The tip section further comprises a multi-element tip electrode mounted at its distal end. The multi-element tip electrode comprises a plurality of electrode members electrically isolated from one another by a non-conductive matrix. The electrode members are arranged such that, during use of the catheter within the heart, at least two different electrode members are capable of contacting the endocardium tissue at one time. A lead wire is electrically connected to each electrode member and extends through the tubing, catheter body and handle.

In a preferred embodiment, the catheter further comprises a rigid, generally tubular housing having proximal and distal ends. The proximal end of the housing is mounted on the distal end of the flexible tubing. The electromagnetic sensor is mounted, at least in part, within the housing. The multi-element tip electrode is mounted at the distal end of the housing.

In one embodiment, the multi-electrode tip electrode comprises a split-tip electrode. The split-tip electrode has a distal portion comprising an external surface and a proximal portion that forms a recessed stem. The multi-electrode tip electrode comprises a plurality of longitudinally adjacent electrode members, each having an external surface and a recessed stem portion. Each electrode member is electrically connected to an associated electrode lead wire and electrically isolated from adjacent electrode members.

In another embodiment, the multi-element tip electrode comprises a non-conductive base made of a generally rigid material having a generally closed rounded distal end and an open proximal end. The electrode members are electrically isolated from one another by a non-conductive matrix overlying the non-conductive base. The lead wires electrically-connected to the electrode members extend through holes in the non-conductive base.

In still another embodiment, the invention is directed to a system for determining the direction and/or velocity of electrical activity in the heart. The system comprises a catheter as described above in combination with a means for receiving, analyzing and displaying information concerning the location of the catheter tip section and of the electrical activity in heart and information concerning the direction and/or velocity of the electrical activity in the heart. The means is electrically connected to the electrode lead wires and to the sensor cable.

In yet another embodiment, the invention is directed to a method for determining the direction and/or velocity of electrical activity in the heart chamber. A system is provided, as described above. The catheter is inserted into the heart. The distal end of the tip section is contacted with heart tissue whereby at least two, and preferably at least three, electrode members are in contact with the myocardium. The location of the myocardium in contact with the electrode members is determined, as well as the direction and/or velocity of the electrical activity at that location. Additionally, one can use this method to map the shape and electrical activity of the heart chamber by repeatedly contacting the tip section with the heart wall, measuring the electrical activity, and recording the location of and electrical activity measured at each position of contact. The recorded positions are displayed on the receiving, analyzing and displaying means to provide a map of the heart.

DESCRIPTION OF THE DRAWINGS

These and other features and advantages of the present invention will be better understood by reference to the following detailed description when considered in conjunction with the accompanying drawings wherein.

DETAILED DESCRIPTION

In a particularly preferred embodiment of the invention, there is provided a multi-electrode catheter for mapping the direction and velocity of electrical current in the heart. As shown in FIGS. 1–4, catheter 10 comprises an elongated catheter body 12 having proximal and distal ends, a tip section 14 at the distal end of the catheter body 12, and a control handle 16 at the proximal end of the catheter body 12.

Figure 1:
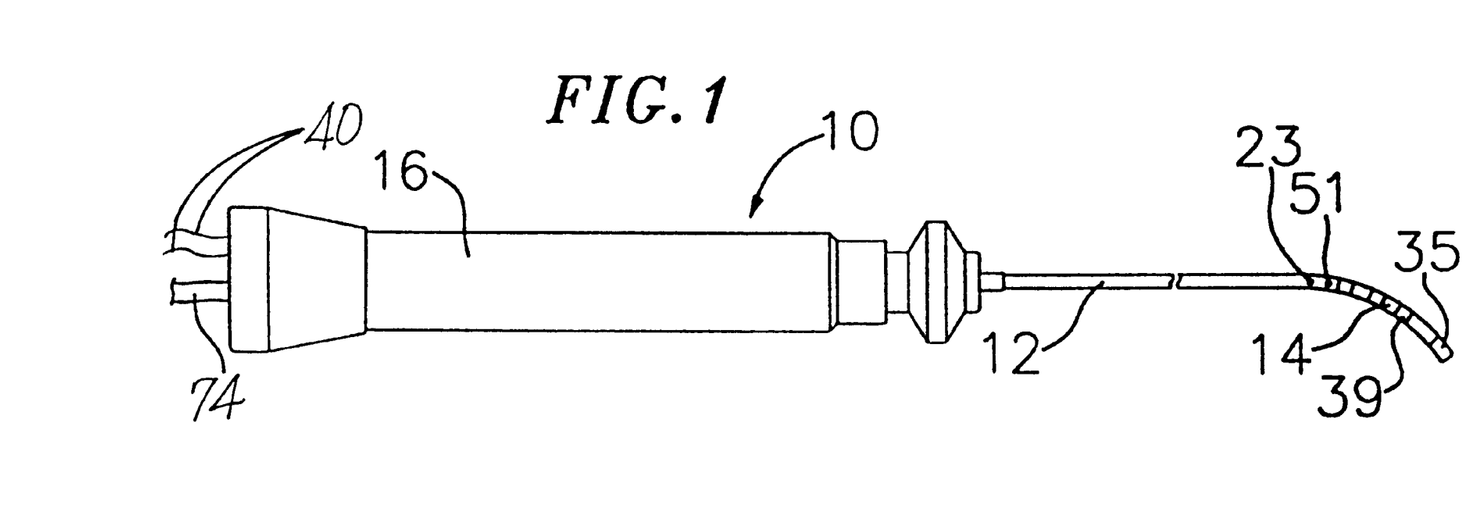
FIG. 1 is a side view of an embodiment of the catheter of the invention.
Figure 2A:
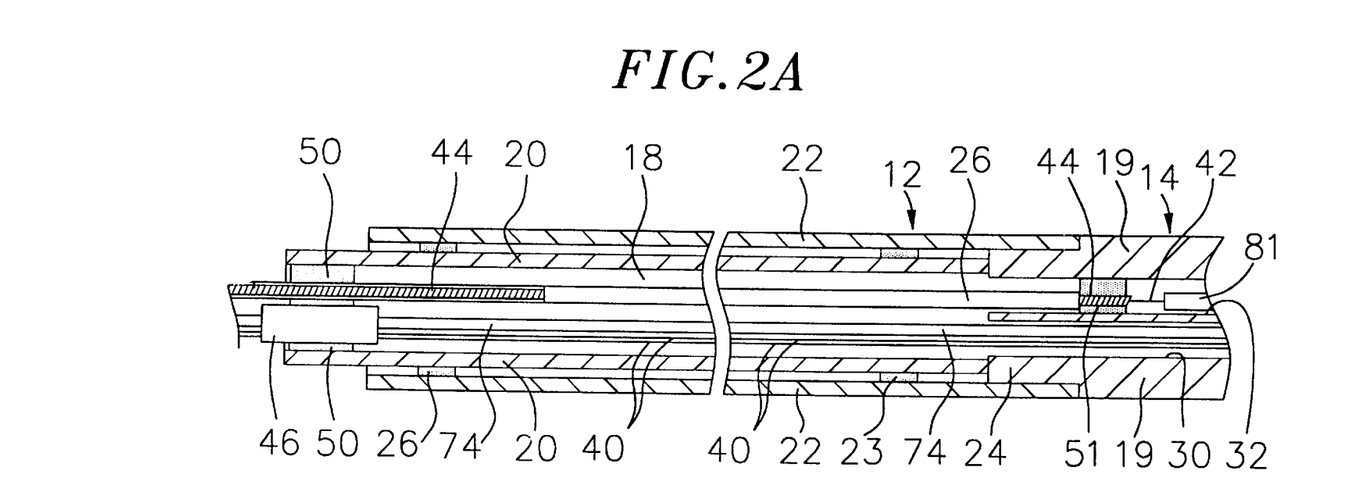
FIG. 2A is a side cross-sectional view of the catheter body showing one method for mounting the tip section to the body.

With reference to FIG. 2A, the catheter body 12 comprises an elongated tubular construction having a single, central or axial lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner.

The outer diameter of the catheter body 12 is not critical, but is preferably no more than about 8 french. Likewise the thickness of the outer wall 22 is not critical. The inner surface of the outer wall 22 is lined with a stiffening tube 20, which can be made of any suitable material, preferably polyimide. The stiffening tube, along with the braided outer wall 22, provides improved torsional stability while at the same time minimizing the wall thickness of the catheter body. The outer diameter of the stiffening tube 20 is about the same as or slightly smaller than the inner diameter of the outer wall 22. The gap depicted in FIGS. 2A and 2B between the outer wall 22 and stiffening tube 20 is shown only for purposes of depicting the glue joints. Polyimide tubing is presently preferred because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

A particularly preferred catheter has an outer wall 22 with an outer diameter of about 0.092 inch and an inner diameter of about 0.063 inch and a polyimide stiffening tube 20 having an outer diameter of about 0.062 inch and an inner diameter of about 0.052 inch.

As shown in FIG. 2A, the tip section 14 comprises a short section of tubing 19 having two lumens 30 and 32. The tubing 19 is made of a suitable non-toxic material which is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 french. The size of the lumens 30 and 32 is not critical. In a particularly preferred embodiment, the tip section has an outer diameter of about 7 french (0.092 inch).

Any suitable method for attaching the catheter body 12 to the tip section 14 can be used. One such method is illustrated in FIG. 2A. The proximal end of the tip section 14 comprises an outer circumferential notch 24 that receives the inner surface of the outer wall 22 of the catheter body 12. The tip section 14 and catheter body 12 are attached by glue or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint 23 with polyurethane flue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g., Super Glue™. Thereafter, a second glue joint 26 is formed between the proximal ends of the stiffening tube 20 and the outer wall 22 using a slower drying but stronger glue, e.g., polyurethane.

If desired, a spacer can be located within the catheter body between the distal end of the stiffening tube and the proximal end of the tip section. The spacer, preferably made of Teflon®, provides a transition in flexibility at the junction of the catheter body and tip section, which allows this junction to bend smoothly without folding or kinking. A catheter having such a spacer is described, for example, in U.S. Patent No. 5,964,757, entitled "Steerable Direct Myocardial Revascularization Catheter", the disclosure of which is incorporated herein by reference.

Figure 2B:
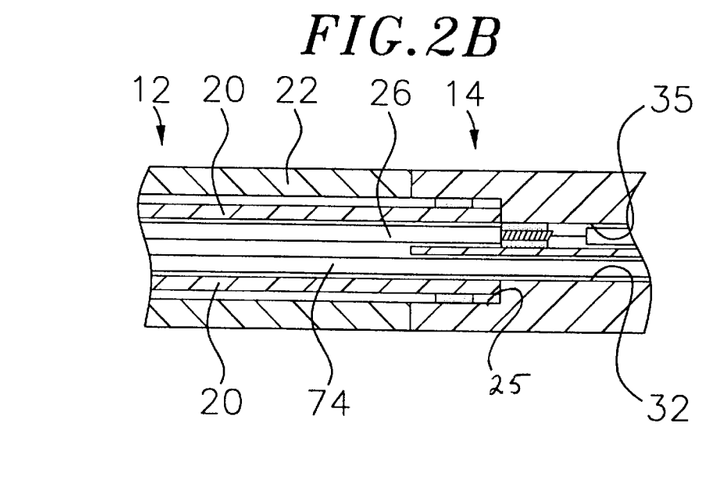
FIG. 2B is a side cross-sectional view of the catheter body showing an alternative method for mounting the tip section to the body.

Alternatively, as shown in FIG. 2B, a recess 25 is provided at in the proximal end of tubing 19 forming the tip section 14. The recess 25 has a diameter slightly greater than the outer diameter of the stiffening tube 20 and preferably has a depth of about 3.5 mm. The stiffening tube 20 extends beyond the distal end of the outer wall 22 of the catheter body and into the recess 25 in the tubing 19 of the tip section. The stiffening tube 20 can be held in place in the recess 25 by polyurethane glue or the like.

A puller wire 42 extends through the single lumen 18 of the catheter body 12. The puller wire 42 is anchored at its proximal end to the control handle 16 and anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

A compression coil 44 extends from the proximal end of the catheter body 12 to the proximal end of the tip section 14 in surrounding relation to the puller wire 42. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.009 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and any of the lead wires 40 or sensor cable 74. A non-conductive sheath 26 made of polyimide tubing is presently preferred.

The compression coil 44 is anchored at its proximal end to the proximal end of the stiffening tube 20 in the catheter body 12 by glue joint 50 and at its distal end to the tip section 14 by glue joint 51. Both glue joints 50 and 51 preferably comprise polyurethane glue or the like. The glue may be applied by means of a syringe or the like through a hole made between the outer surface of the catheter body 12 and the single lumen 18. Such a hole may be formed, for example, by a needle or the like that punctures the wall of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

The distal end of the puller wire 42 extends into the second lumen 32 of the tip section 14. Within the tip section 14, the puller wire 42 extends into a plastic, preferably Teflon®, sheath 81, which prevents the puller wire 42 from cutting into the wall of the tip section 14 when the tip section 14 is deflected. Alternatively, the compression coil 44 may extend distally into the tip section 14 beyond glue joint 51. The turns of the portion of the compression coil beyond the glue joint 51 are expanded longitudinally and are thus bendable and compressible. Such an expanded portion of the compression coil 44, also prevents the puller wire from cutting into the wall of the tip section 14 is described for example in U.S. Pat. No. 5,431,168 which is incorporated herein by reference.

Figure 10:
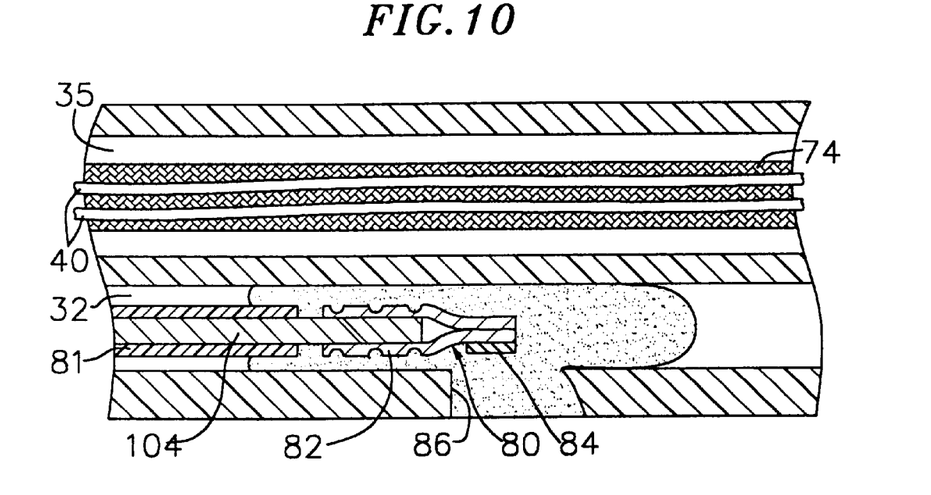
FIG. 10 is a cross-sectional view of a portion of the catheter tip section showing a preferred means for anchoring the puller wire.
Figure 11:
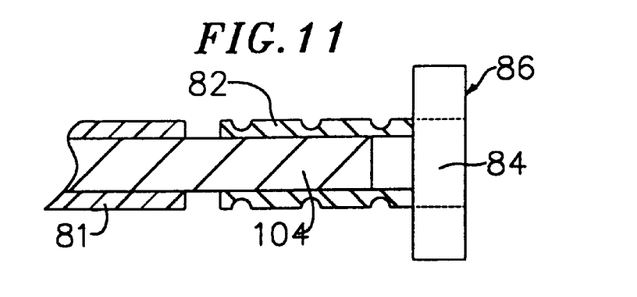
FIG. 11 is a top cross-sectional view of a preferred puller wire anchor.
Figure 12:
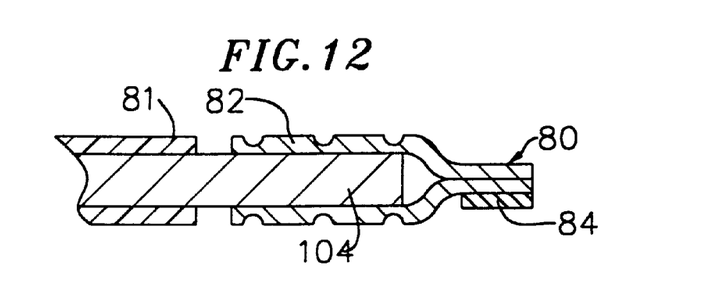
FIG. 12 is a side cross-sectional view of a preferred puller wire anchor.

The distal end of the puller wire 42 may be anchored to the side wall of the tip section 14 or to the end of tubing 19 or to a tip electrode member. A preferred means for anchoring the puller wire 42 to the side wall comprises an anchor 80 fixedly attached to the distal end of the puller wire 42, as illustrated in FIGS. 10–12. In such an embodiment, the anchor is formed by a metal tube 82, e.g., a short segment of hypodermic stock, which is fixedly attached, e.g., by crimping, to the distal end of the puller wire 42. The tube 82 has a section which extends a short distance beyond the distal end of the puller wire 42. A crosspiece 84 made of a small section of stainless steel ribbon or the like is soldered or welded in a transverse arrangement to the distal end of the tube 82, which is flattened during the operation. This creates a T-bar anchor 80. A notch 86 is created in the side of the catheter tip section 14 resulting in an opening into the second lumen 32 carrying the puller wire 42. The anchor 80 lies within the notch 86. Because the length of the ribbon forming the cross-piece 84 is longer than the diameter of the opening into the second lumen 32, the anchor 80 cannot be pulled completely into the second lumen 32. The notch 86 is then sealed with polyurethane or the like to give a smooth outer surface.

Figure 13:
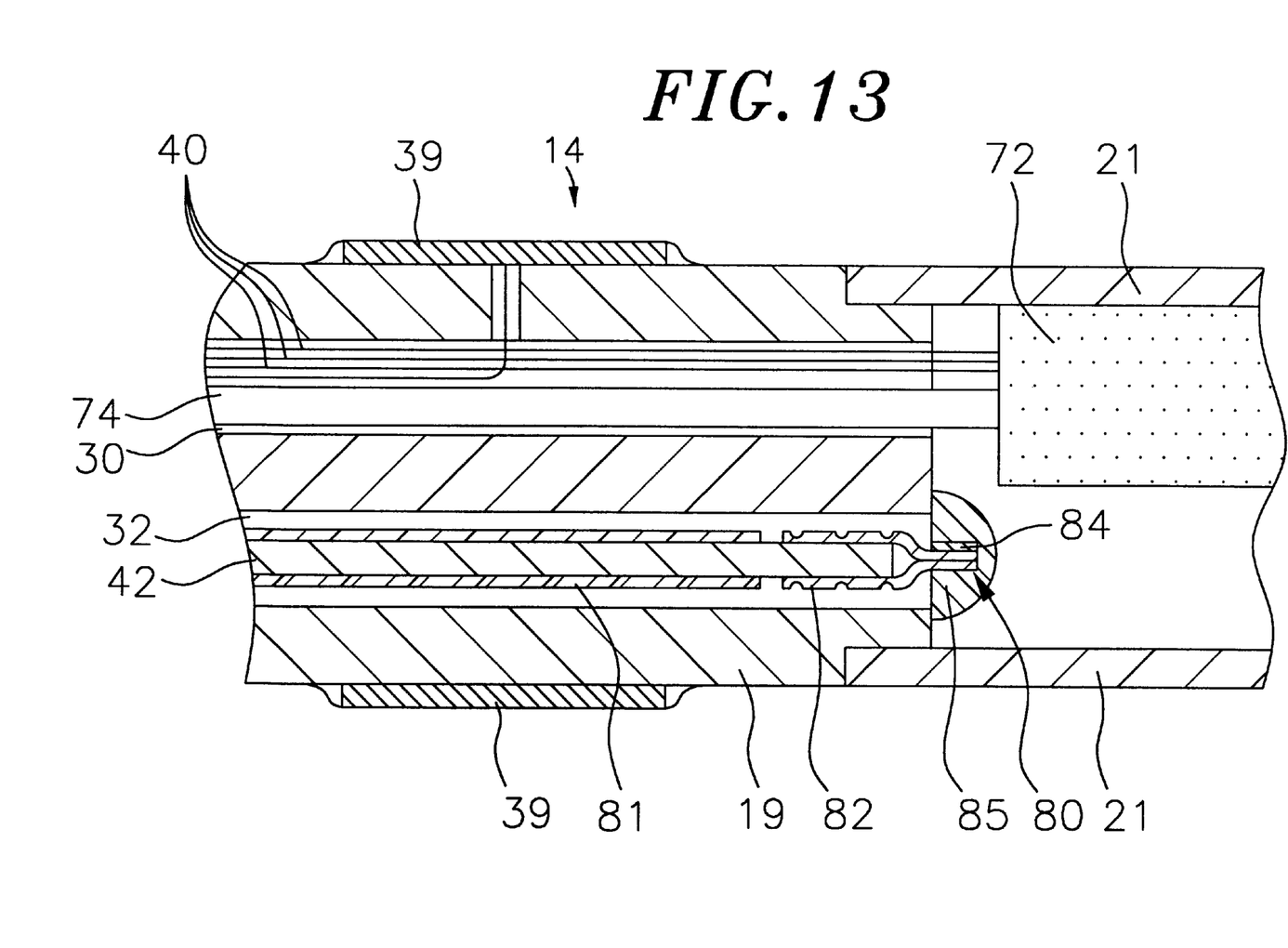
FIG. 13 is a cross-sectional view of a portion of the catheter tip section showing an alternate means for anchoring the puller wire.

FIG. 13 depicts an alternative embodiment where the puller wire 42 extends to the distal end of the second lumen 32. The cross-piece 84 is fixed at this position by a polyurethane cap 85, which also seals the distal end of the second lumen 32. Because the cross-piece 84 is larger than the diameter of the second lumen 32, the anchor 80 cannot be pulled back into the second lumen when the tip section 14 is deflected.

Figure 3A:
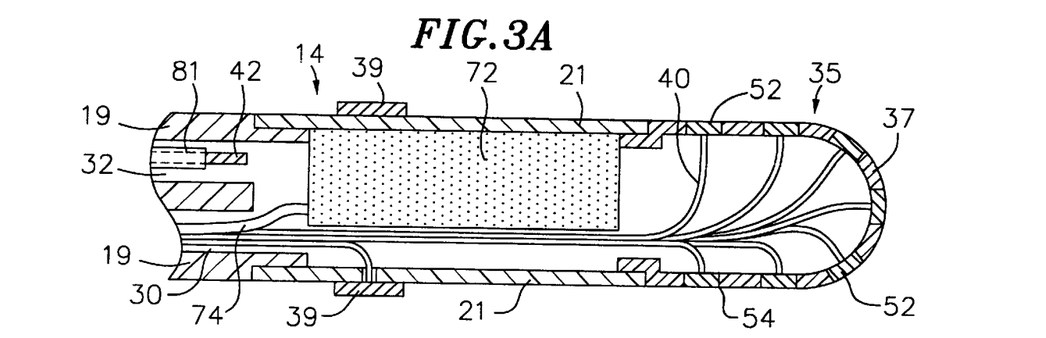
FIG. 3A is a side cross-sectional view of the catheter tip section showing one embodiment of a multi-element tip electrode.
Figure 3B:
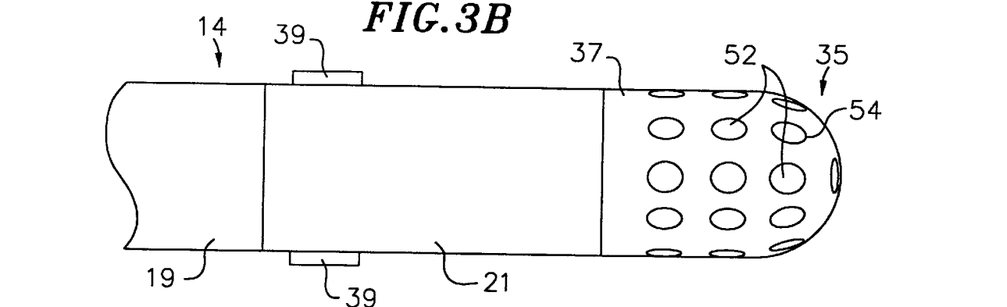
FIG. 3B is a side view of the catheter tip section of FIG. 3A.

With reference to FIGS. 3A and 3B, at the distal end of the tubing 19 of the tip section 14 is a nonconductive housing 21, preferably made of a generally rigid plastic such as polyetheretherketone (PEEK). The housing 21 is generally cylindrical in shape, having a diameter similar to that of the tubing 19, and is bonded with polyurethane glue or the like to the distal end of the tubing 19. The lumens 30 and 32 end at the distal end of the tubing 19 and are in open communication with the interior of the housing 21.

At the distal end of the housing 21 is a multi-element tip electrode 35. The multi-element tip electrode 35 comprises a non-conductive matrix 37 having a plurality of holes 54. The non-conductive matrix 37 can be made of any suitable material, for example, PEEK, and is attached to the housing 21 by any suitable method, for example, using polyurethane glue. Within the non-conductive matrix 37, electrode members 52 are mounted. Each electrode member 52 is cylindrically shaped, having a generally round cross-sectional area. The electrode members 52 can alternatively have any other suitable shape, such as square, rectangular or oval. A minimum surface area of about one square millimeter is presently preferred. The exterior face of each electrode member 52 is generally flush with the exterior surface of the non-conductive matrix 37. Similarly, the inner face of each electrode member 52 is generally flush with the interior surface of the non-conductive matrix 37. The electrode members 52 are fixed within the holes 54 of the non-conductive matrix 37 by any suitable method, for example, by polyurethane glue or the like. The electrode members 52 are arranged about the non-conductive matrix 37 such that when the tip section 14 comes in contact with the myocardium, at least two, and preferably three, electrode members 52 typically make contact with the tissue. As discussed in more detail below, this design permits measurement of the direction and velocity of electrical impulses propagating in the myocardium.

Figure 4:
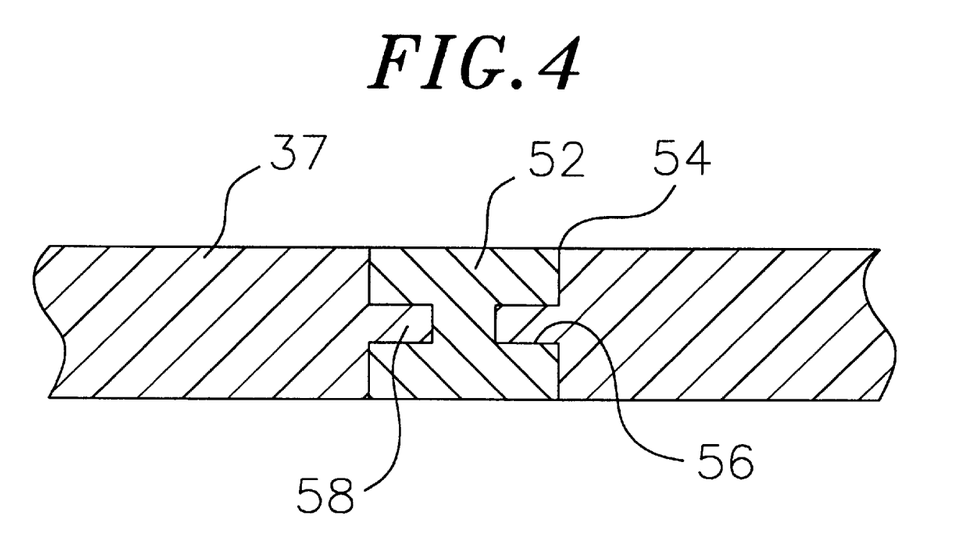
FIG. 4 is a cross-sectional view of the non-conductive matrix of the multi-element tip electrode of FIG. 3A on which is mounted an electrode member.

Another method for fixing the electrode members 52 within the non-conductive matrix 37 is shown in FIG. 4. Between the exterior and interior faces of the electrode member 52 is a circumferential notch 56. Within each hole 54 in the non-conductive matrix 37 is a corresponding circumferential flange 58. Each electrode member 52 is snapped into a hole 54 so that the flange 58 mates with the notch 56 of the electrode member 52, keeping the electrode member in place within the non-conductive matrix 37. Polyurethane glue or the like is preferably used in conjunction with this design to assure liquid tightness.

The electrode members 52 are each connected to a separate electrode lead wire 40. The electrode lead wires 40 are electrically connected to the interior face of each of the electrode members 52 by any suitable method, for example, by solder or the like. The electrode lead wires 40 extend through the interior of the housing 21, through the first lumen 30 of the tubing 19 of the tip section, through the single lumen 18 of the catheter body 12, and finally through the control handle 16. The lead wires 40 terminate in their proximal end in an input jack (not shown) that may be plugged into an appropriate monitor (not shown). The portion of the lead wires 40 extending through the catheter body 12 may be enclosed within a protective sheath if desired.

An electromagnetic sensor 72 is contained within the distal end of the tip section 14. In the depicted embodiment, the sensor 72 is mounted within the housing 21. The sensor 21 is fixed within the housing 21 by any suitable method, for example, using polyurethane glue or the like.

The electromagnetic sensor 72 is electrically connected to an electromagnetic sensor cable 74, which extends through the first lumen 30 of the tip section 14, through the catheter body 12, and into the control handle 16. The electromagnetic sensor cable 74 comprises multiple wires encased within a plastic covered sheath. Within the catheter body 12, the sensor cable 74 may be enclosed within a protective sheath along with the electrode lead wires, if desired. In the control handle 16, the wires of the sensor cable 74 are connected to a circuit board 64. The circuit board 64 amplifies the signal received from the electromagnetic sensor 72 and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice.

A suitable electromagnetic sensor is described, for example, in U.S. Pat. No. 4,391,199, which is incorporated herein by reference. A preferred electromagnetic mapping sensor 72 is manufactured by Biosense Ltd. Israel and marketed under the trade designation NOGA.

To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the DMR catheter containing a second electromagnetic sensor is advanced into the patient's heart. Each sensor comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed. The sensor can also detect displacement of that catheter that is caused by contraction of the heart muscle. A preferred mapping system includes a catheter comprising multiple electrodes and an electromagnetic sensor, such as the NOGA-STAR catheter marketed by Cordis Webster, Inc., and means for monitoring and displaying the signals received from the electrodes and electromagnetic sensor, such as the Biosense-NOGA system, also marketed by Cordis Webster, Inc.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved. By combining the electromagnetic sensor and electrodes members, a physician can simultaneously map the contours or shape of the heart chamber and the electrical activity of the heart. Additionally, by having at least two, and preferably at least three, electrode members in contact with the myocardium, the intensity, direction and velocity of the propagation of electrical signals in the heart can be determined.

If desired, one or more ring electrodes 39 can also be mounted on the housing 21 or tubing 19 of the tip section 14. Each ring electrode 39 is slid over the housing 21 or tubing 19 and fixed in place by glue or the like. Electrode lead wires 40 are attached to the ring electrodes 39 by any conventional technique. Connection of a lead wire 40 to a ring electrode 39 is preferably accomplished by first making a small hole through the housing 21 or tubing 19. Such a hole can be created, for example, by inserting a needle through the housing 21 or tubing 19 and heating the needle sufficiently to form a permanent hole. A lead wire 40 is then drawn through the hole by using a microhook or the like. The ends of the lead wire 40 are then stripped of any coating and soldered or welded to the underside of the ring electrode 39, which is then slid into position over the hole and fixed in place with polyurethane glue or the like.

Figure 5:
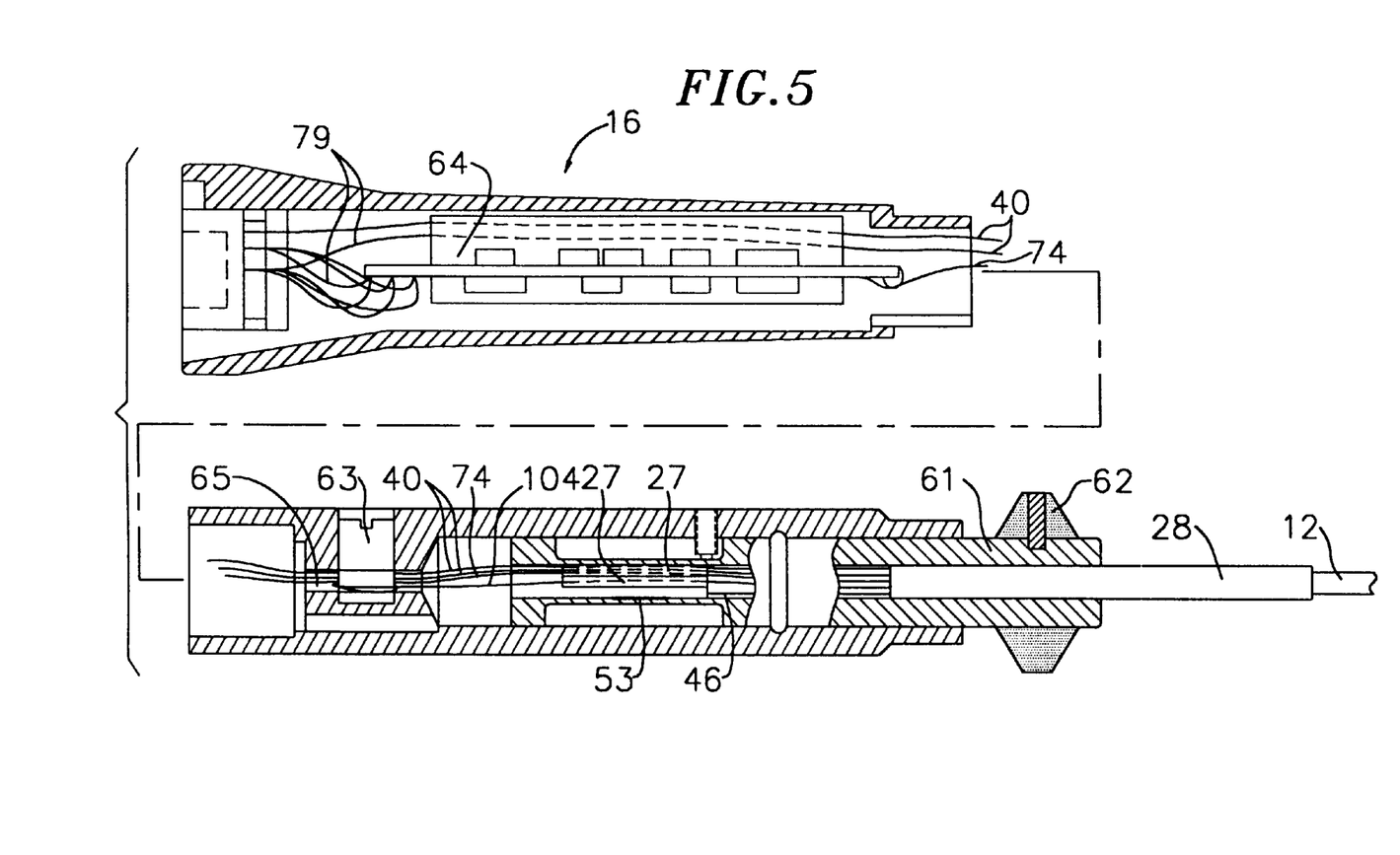
FIG. 5 is a side cross-sectional view of the catheter handle.

The electrode lead wires 40 and electromagnetic sensor cable 74 should be allowed some longitudinal movement within the catheter body so that they do not break when the tip section 14 is deflected. To provide for such lengthwise movement, there may provided a tunnel through the glue joint 50, which secures the proximal end of the compression coil 44 inside the catheter body 12. The tunnel can be formed, for example, by a transfer tube 46, preferably made of short segments of polyimide tubing, through which the lead wires 40 and sensor cable 72 can pass. Longitudinal movement of the puller wire 42 relative to the catheter body 12, which results in deflection of the tip section 12, is accomplished by suitable manipulation of the control handle 16. As shown in FIG. 5, the distal end of the control handle 16 comprises a piston 61 with a thumb control 62 for manipulating the puller wire 42. The proximal end of the catheter body 12 is connected to the piston 61 by means of a shrink sleeve 28.

The puller wire 42, lead wires 40 and electromagnetic sensor cable 74 extend through the piston 61. The puller wire 42 is anchored to an anchor pin 63, located proximal to the piston 61. The lead wires 40 and electromagnetic sensor cable 74 extend past the anchor pin 63 though a tunnel 65, located near the side of the control handle 16. If desired, the lead wires 40 and sensor cable 74 can be contained within a protective sheath within the control handle 16. The electromagnetic sensor cable 74 connects to the circuit board 64 in the proximal end of the control handle 16. Wires 79 connect the circuit board 64 to a computer and imaging monitor (not shown). If desired, the circuit board 64 can be contained in a separate sensor control module (not shown) outside of the control handle 16, in which case the sensor cable 74 extends out the proximal end of the control handle 16 to the sensor control module.

Figure 3C:
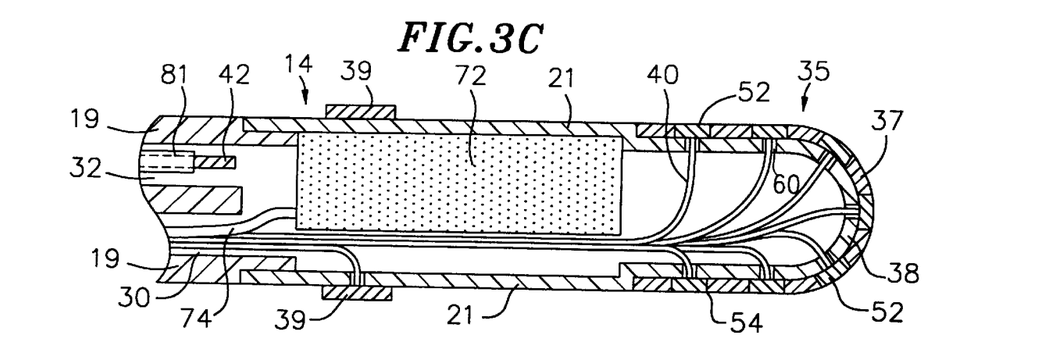
FIG. 3C is a side cross-sectional view of the catheter tip section showing an alternative embodiment of a multi-element tip electrode.

In an alternative embodiment, shown in FIG. 3C, mounted at the distal end of the housing 21 is a non-conductive base 38. The non-conductive base 38 comprises a plurality of lead wire holes 60. The non-conductive base 38 can be made of any suitable material, for example, PEEK, and is attached to the housing 21 by any suitable method, for example, using polyurethane glue. Alternatively, the housing 21 and non-conductive base 38 may be formed as a single unit from the same material. The multi-element tip electrode 35, comprising a nonconductive matrix 37 and electrode members 52 as described above, overlies the non-conductive base 37 and fits snugly thereto. The holes 54 of the non-conductive matrix 37 are aligned with the lead wire holes 60 in the base 38 such that the lead wires 40 attached to the electrode members 52 extend through the lead wire holes 60 in the non-conductive base 38.

Another preferred embodiment of the present invention is depicted in FIGS. 6 to 9. The multi-element tip electrode is in the form of a split-tip electrode. As in the embodiment described above, a generally-tubular, cylindrical, nonconductive housing 21 is attached to the distal end of the tubing 19 of the tip section 14. An electromagnetic sensor 72 is mounted within the housing 21. The multi-element tip electrode 35 is mounted on the distal end of the housing 21, as described in more detail below.

The multi-element tip electrode 35 comprises a plurality of electrode elements or members 88. In the depicted embodiment, the multi-element tip electrode 35 comprises four electrode members 88, but may comprise as few as two or three electrode members. The composite electrode 35 can comprise more than four electrode members 88 if desired.

Figure 6:
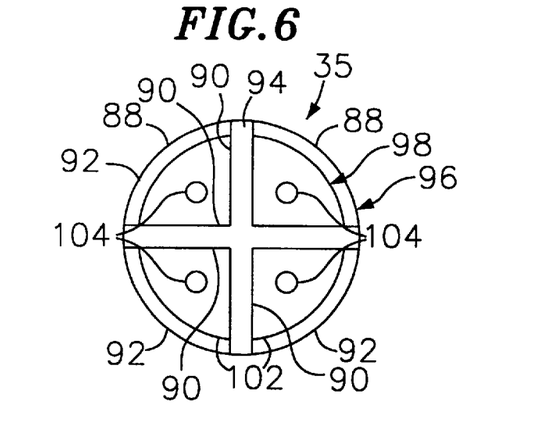
FIG. 6 is a proximal end view of a split-tip multi-element tip electrode.
Figure 7:
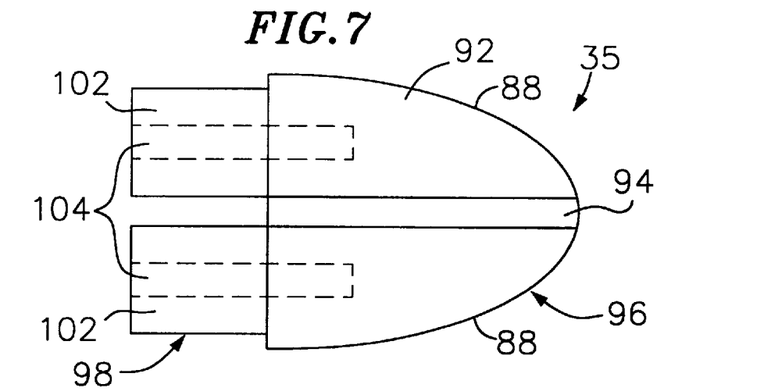
FIG. 7 is side view of the split-tip multi-element tip electrode of FIG. 6.
Figure 8:
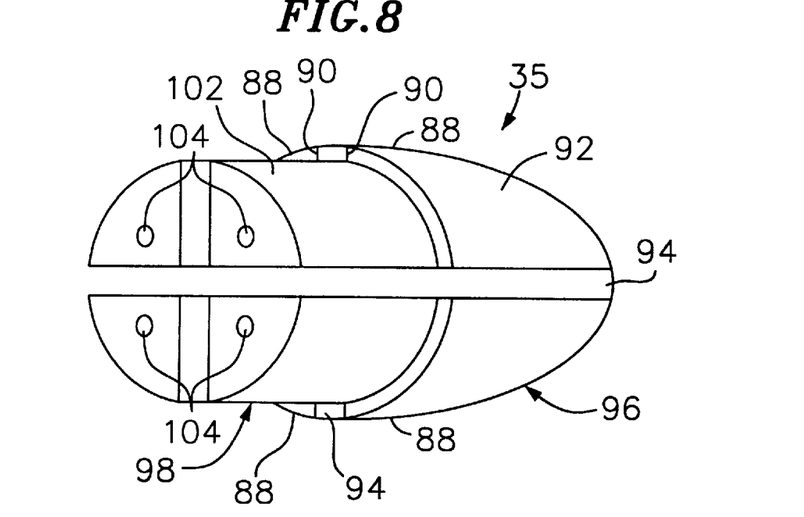
FIG. 8 is rotated view of the split-tip multi-element tip electrode of FIG. 6.

Each electrode member 88 has two interior sides 90 and an exterior surface 92. The electrode members 88 are arranged with each of their respective interior sides 90 adjacent to the interior sides of two adjacent electrode members so that each electrode member 88 forms a quadrant of the multi-element tip electrode. The electrode members 88 are electrically isolated from one another by an insulating material 94. Each of the electrode members 88 can be of any suitable construction and are preferably made of platinum or alloys of platinum and iridium.

Figure 9:
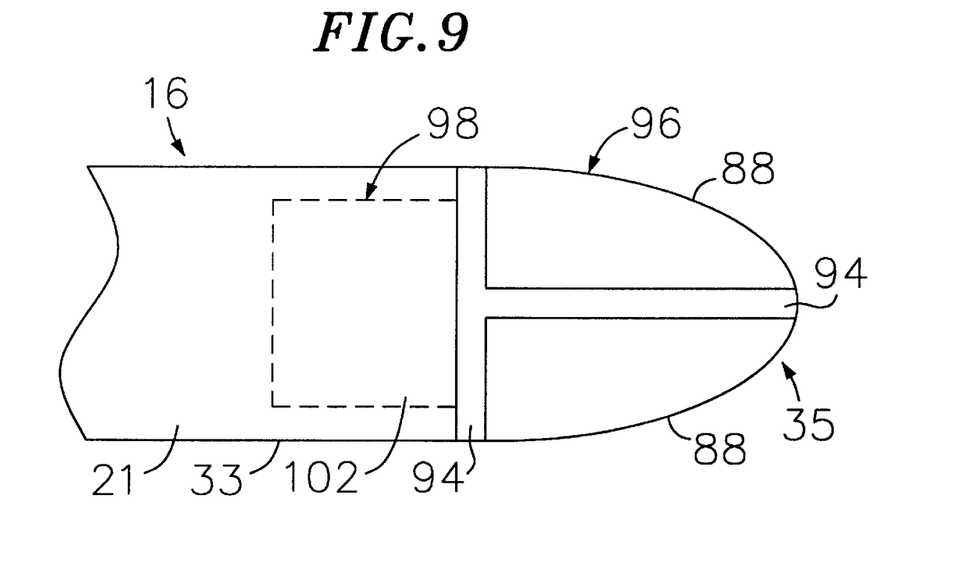
FIG. 9 is side view of the catheter tip section showing the split-tip multi-element tip electrode mounted to the housing.

The multi-element tip electrode 35 has a distal section 96 and a proximal section 98. The distal section 96 has an exterior surface which is exposed to the heart tissue. The distal section 96 can be of any suitable shape, e.g., rounded, cylindrical with a rounded distal end, or generally bullet-shaped. The precise shape of the distal section 96 is not critical so long as the design permits three or more electrode members 88 to be in contact with the endocardial tissue.

The proximal section 98 of the multi-element tip electrode 35 forms a recessed stem 102 which is fittedly secured in the distal end of the housing 21. The stem 102 can be secured to the housing 21 by any suitable method, for example, with polyurethane glue or the like.

An electrode lead wire 40 is electrically attached to each electrode member 88. To facilitate this connection, an electrode lead bore 104 is formed in the proximal end of each tip electrode 88. An electrode lead wire 40 is then attached to each electrode member 88 within the electrode lead bore 104 by any suitable method, for example, by solder.

A presently preferred construction of the multi-element tip electrode shown in this embodiment comprises modifying a 7 French tip electrode, part no. 5203-07, manufactured by Cordis Webster Inc., Baldwin, Park, Calif. The tip electrode is machined to the preferred outer dimensions (described further below), the electrode lead bores are drilled into its proximal end, and the tip electrode is cut into four electrode members. A preferred overall length is about 0.120 inch with a margin of about 0.040 inches. A preferred overall diameter is about 0.092 inch. Each electrode lead bore is preferably about 0.016 inch in diameter and about 0.055 inch deep. The axis of each electrode lead bore is about 0.038 inch from the axis of the composite electrode. The preferred depth of the recess surface is about 0.009 inch.

A preferred method of constructing the composite electrode is by machining the 7 French tip electrode to a desired bullet shape with a rounded tip and having an overall length of about 0.210 inch, a diameter of about 0.092 inch, an exterior surface length of about 0.080 inch, and a margin of about 0.040 inch wide and about 0.009 inch deep. The remaining about 0.090 inch on the proximal end is fashioned into a stem with a diameter of about 0.033 inch.

The members are ultrasonically cleaned, and liquid polyurethane is applied to secure the four pieces together, thereby forming the composite tip. The multi-element tip electrode is then cured at 75° C. for a suitable amount of time and post-cured for one hour at 100° C. A number 24 WW collet is used to remove the cured multi-element tip electrode from the holder. A description of a composite electrode useful in the present invention is described in U.S. Pat. No. 5,836,875, entitled "Split-Tip Electrode", the disclosure of which is incorporated herein by reference.

Figures 14, 15:
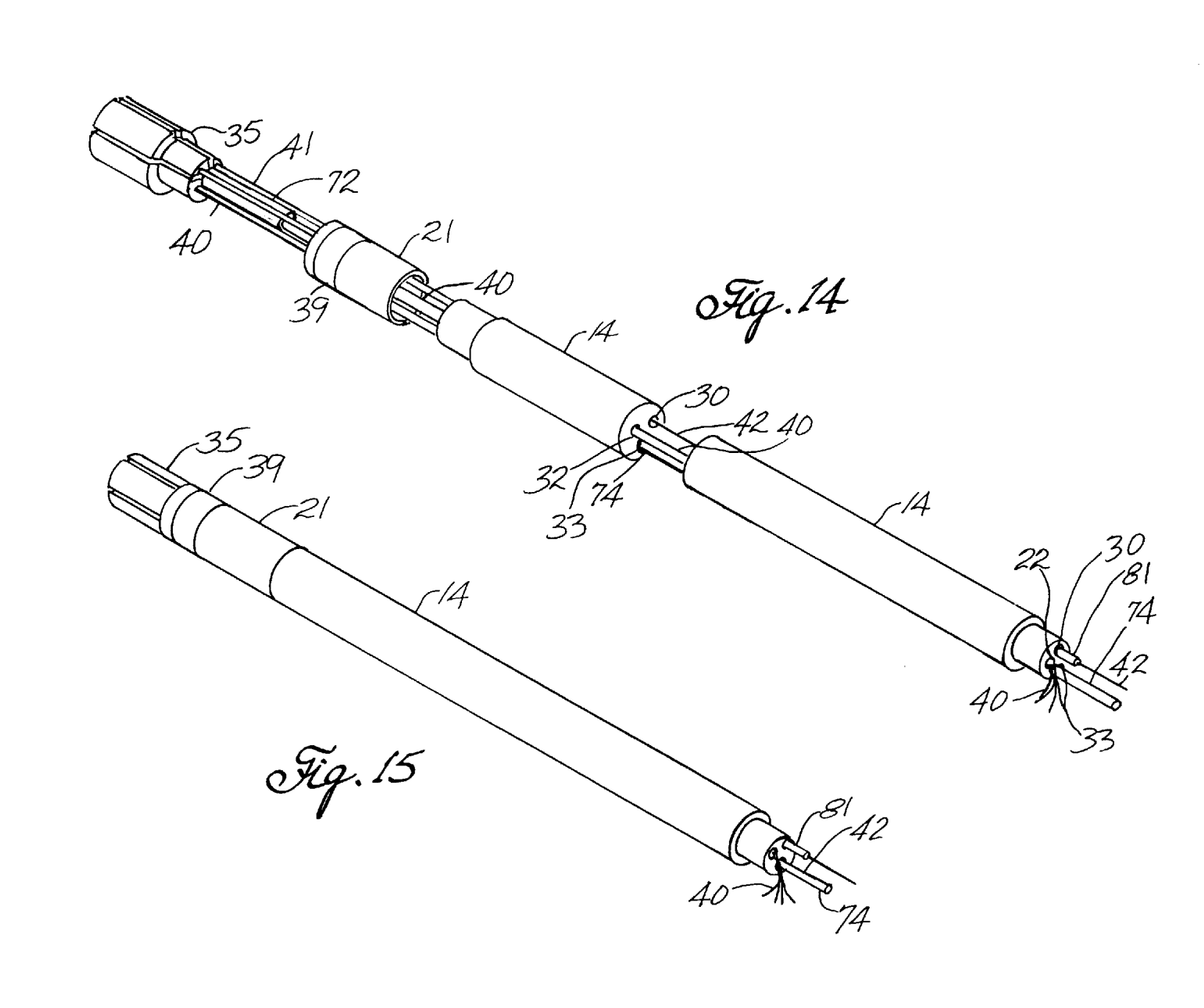
FIGS. 14 and 15 are three-quarter elevational views of an embodiment of a catheter according to the invention having a triple lumen tip section.

Another embodiment of a catheter according to the present invention having a split-tip electrode is shown in FIGS. 13 and 14. The catheter is generally similar to the embodiment described above. The tip section 14 contains three off-axis tip lumens 30, 32 and 33 rather than two. The first lumen 30 contains the puller wire 42 within the sheath 81. The lead wires 40 extend through the second lumen 32. The sensor cable 72 extends within the third lumen 33. In addition to the lead wires 40, safety wires 41 are connected to each electrode member 52 of the composite electrode 35. The safety wires 41 are preferably soldered into the electrode lead bores 104 along with the lead wires 40 and help maintain the multi-element tip electrode 35 in place at the distal end of the tip section 14.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

We claim:

1. A mapping catheter comprising:
   a catheter body having an outer wall, proximal and distal ends and at least one lumen extending therethrough;
   a handle at the proximal end of the catheter body;
   a tip section comprising:
      a flexible tubing having proximal and distal ends and at least one lumen extending therethrough, wherein the proximal end of the flexible tubing is fixedly attached to the distal end of the catheter body;
      an electromagnetic sensor for producing electrical signals indicative of the location of the electromagnetic sensor;
      a multi-element tip electrode mounted at the distal end of the tip section comprising a plurality of cylindrical electrode members electrically isolated from one another by a non-conductive matrix and arranged such that, during use of the catheter within the heart, at least two different electrode members are capable of contacting the endocardium tissue at one time;
   an electromagnetic sensor cable electrically connected to the electromagnetic sensor and extending through the tip section, catheter body and handle for carrying electrical signals from the electromagnetic sensor to a circuit board; and a plurality of electrode lead wires, each lead wire being electrically connected to an electrode member and extending through the tubing, catheter body and handle.

2. A catheter according to claim 1, further comprising a rigid, generally tubular housing having proximal and distal ends, the proximal end being mounted on the distal end of the flexible tubing, and wherein the sensor is mounted, at least in part, within the housing and the multi-element tip electrode is mounted at the distal end of the housing.

3. A catheter according to claim 1, wherein the multi-element tip electrode comprises a plurality of electrode members electrically isolated from one another and arranged such that, during use of the catheter within the heart, at least three different electrode members are capable of contacting the endocardium tissue at one time.

4. A catheter according to claim 1, wherein the non-conductive matrix comprises a rigid material.

5. A catheter according to claim 1, wherein the non-conductive matrix has a generally closed, rounded distal end, a hollow interior, and an open proximal end.

6. A catheter according to claim 1, wherein the multi-element tip electrode comprises:

a non-conductive base made of a generally rigid material having a generally closed, rounded distal end and an open proximal end;

a plurality of electrode members electrically isolated from one another by a non-conductive matrix overlying the nonconductive base, said electrode members being electrically connected to a corresponding electrode lead wire, each lead wire extending through a hole in the non-conductive base.

7. A system for determining the direction and/or velocity of electrical activity in a heart, the system including:

(a) a mapping catheter comprising:

a catheter body having an outer wall, proximal and distal ends and at least one lumen extending therethrough;

a handle at the proximal end of the catheter body;

a tip section comprising:

a flexible tubing having proximal and distal ends and at least one lumen extending therethrough, wherein the proximal end of the flexible tubing is fixedly attached to the distal end of the catheter body;

an electromagnetic sensor for producing electrical signals indicative of the location of the electromagnetic sensor;

a multi-element tip electrode mounted at the distal end of the tip section comprising a plurality of electrode members electrically isolated from one another by a non-conductive matrix and arranged such that, during use different electrode members are capable of contacting the endocardium tissue at one time;

an electromagnetic sensor cable electrically connected to the electromagnetic sensor and extending through the tip section, catheter body and handle for carrying electrical signals from the electromagnetic sensor to a circuit board; and a plurality of electrode lead wires, each lead wire being electrically connected to an electrode member and extending through the tubing, catheter body and handle;

(b) means for receiving, analyzing and displaying information concerning the location of the catheter tip section and of the electrical activity in the heart, and information concerning the direction and/or velocity of the electrical activity in the heart, the means being electrically connected to the electrode lead wires and to the sensor cable.

8. A method for determining the direction and/or velocity of electrical activity in a heart chamber, comprising:

(a) providing a mapping catheter comprising:

a catheter body having an outer wall, proximal and distal ends and at least one lumen extending therethrough;

a handle at the proximal end of the catheter body;

a tip section comprising:

a flexible tubing having proximal and distal ends and at least one lumen extending therethrough, wherein the proximal end of the flexible tubing is fixedly attached to the distal end of the catheter body;

an electromagnetic sensor for producing electrical signals indicative of the location of the electromagnetic sensor;

a multi-element tip electrode mounted at the distal end of the tip section comprising a plurality of electrode members electrically isolated from one another by a non-conductive matrix and arranged such that, during use of the catheter within the heart, at least two different electrode members are capable of contacting the endocardium tissue at one time;

an electromagnetic sensor cable electrically connected to the electromagnetic sensor and extending through the tip section, catheter body and handle for carrying electrical signals from the electromagnetic sensor to a circuit board; and a plurality of electrode lead wires, each lead wire being electrically connected to an electrode member and extending through the tubing, catheter body and handle;

(b) inserting the catheter into the heart and contacting the distal end of the tip section with heart tissue whereby at least two electrode members are in contact with a location of the myocardium;

(c) determining the location of the myocardium in contact with the at least two electrode members and the direction and/or velocity of the electrical activity at that location.

9. A method according to claim 8, wherein at least three electrode members are in contact with the tissue.

10. A method according to claim 8, further comprising mapping the shape and electrical activity of the heart chamber by:

(a) advancing the catheter tip section into the heart chamber;

(b) repeatedly contacting the tip section with the heart wall, measuring the electrical activity, recording the location of and electrical activity measured at each position of contact; and (c) displaying the recorded positions on the receiving, analyzing and displaying means.

11. A method according to claim 10, wherein at least three electrode members are in contact with the tissue.

12. A method according to claim 8 comprising:

determining the location of the myocardium in contact with the at least two electrode members and the velocity of the electrical activity at that location.

* * * * *

UNITED STATES PATENT AND TRADEMARK OFFICE
CERTIFICATE OF CORRECTION

PATENT NO. : 6,064,905
DATED : May 16, 2000
INVENTOR(S) : Wilton W. Webster, Jr.; Dean M. Ponzi It is certified that error appears in the above-identified patent and that said Letters Patent is hereby corrected as shown below:

Column 11,
Line 54, replace "during use different" with -- during use of the catheter within the heart, at least two different --.

Signed and Sealed this

Fifth Day of February, 2002

Attest:

JAMES E. ROGAN
*Attesting Officer*     *Director of the United States Patent and Trademark Office*